United States Patent [19]

Young et al.

[11] Patent Number: 5,300,081

[45] Date of Patent: Apr. 5, 1994

[54] SURGICAL CLIP APPLIER HAVING CLIP ADVANCEMENT CONTROL

[75] Inventors: Wayne P. Young, Brewster, N.Y.; Dominick L. Mastri, Bridgeport; Henry Bolanos, East Norwalk, both of Conn.

[73] Assignee: United States Surgical Corporation, Norwalk, Conn.

[21] Appl. No.: 959,190

[22] Filed: Oct. 9, 1992

[51] Int. Cl.$^5$ .............................................. A61B 17/00
[52] U.S. Cl. .................................. 606/143; 606/139; 606/142; 227/901
[58] Field of Search ....................... 606/147, 143, 139; 227/19, 901, 275–177, 181–182; 29/243.56

[56] References Cited

U.S. PATENT DOCUMENTS

| D. 276,650 | 12/1984 | Green et al. |
| 2,008,367 | 7/1935 | Rhinevault |
| 2,741,248 | 4/1956 | Woodhall |
| 2,968,041 | 1/1961 | Skold |
| 3,585,985 | 6/1971 | Gould |
| 3,603,310 | 9/1971 | Mottin et al. |
| 3,631,707 | 1/1972 | Miller |
| 3,777,538 | 12/1973 | Weatherly et al. |
| 3,834,392 | 9/1974 | Lampman et al. |
| 3,848,773 | 11/1974 | Adler et al. |
| 3,856,016 | 12/1974 | Davis |
| 3,870,048 | 3/1975 | Yoon |
| 3,882,854 | 5/1975 | Hulka et al. |
| 3,954,108 | 5/1976 | Davis |
| 3,955,581 | 5/1976 | Spasiano et al. |
| 3,989,049 | 11/1976 | Yoon |
| 4,027,510 | 6/1977 | Hiltebrandt |
| 4,038,987 | 8/1977 | Komiya |
| 4,064,881 | 12/1977 | Meredith |
| 4,084,594 | 4/1978 | Mosior |
| 4,085,743 | 4/1978 | Yoon |
| 4,101,063 | 7/1978 | Kapitanov et al. |
| 4,103,680 | 8/1978 | Yoon |
| 4,152,920 | 5/1979 | Green |
| 4,166,466 | 9/1979 | Jarvik |
| 4,169,476 | 10/1979 | Hiltebrandt |
| 4,185,762 | 1/1980 | Froehlich |
| 4,188,953 | 2/1980 | Klieman et al. |
| 4,196,836 | 4/1980 | Becht |
| 4,226,239 | 10/1980 | Polk et al. |
| 4,226,242 | 10/1980 | Jarvik |
| 4,228,895 | 10/1980 | Larkin |
| 4,230,116 | 10/1980 | Watson |
| 4,240,411 | 12/1980 | Hosono |
| 4,242,902 | 1/1981 | Green |
| 4,246,903 | 1/1981 | Larkin |
| 4,257,419 | 3/1981 | Göltner et al. |
| 4,273,129 | 6/1981 | Boebel |
| 4,296,751 | 10/1981 | Blake, III et al. |

(List continued on next page.)

FOREIGN PATENT DOCUMENTS

| 0406724 | 1/1991 | European Pat. Off. |
| 0409569 | 1/1991 | European Pat. Off. |
| 2330182 | 1/1975 | Fed. Rep. of Germany |
| 2546696 | 4/1976 | Fed. Rep. of Germany |
| 3802651 | 8/1989 | Fed. Rep. of Germany |
| 8910094 | 11/1989 | PCT Int'l Appl. |
| 9003763 | 4/1990 | PCT Int'l Appl. |
| 1093329 | 5/1984 | U.S.S.R. |
| 2054384 | 7/1979 | United Kingdom |

U.S. PATENT DOCUMENTS

Richard Wolf Instrument Manual, 1985.
Information Booklet for Auto Suture ® Premium Surgiclip ® Clip Applier 1989.
Information Booklet for Auto Suture ® Skin and Fascia Surgical Stapling Instruments, 1981.

(List continued on next page.)

Primary Examiner—Stephen C. Pellegrino
Assistant Examiner—Jeffrey A. Schmidt

[57] ABSTRACT

An apparatus is disclosed for applying surgical clips which comprises a handle portion, a body portion which extends distally from the handle portion, jaw members positioned adjacent the distal end of the body portion for receiving and subsequently forming a clip, camming means which are operable from the handle portion for camming the jaw members closed to form a clip, storage means for storing a plurality of surgical clips in a position for individual advancement to the jaw members, clip advancement means for individually advancing the clips from the storage means into the jaw members, and control means for selecting between a first mode of operation in which the advancement of a clip from the storage means into the jaw members is initiated by the user and a second mode in which it is initiated independent of the user.

12 Claims, 7 Drawing Sheets

U.S. PATENT DOCUMENTS

| | | |
|---|---|---|
| 4,299,224 | 11/1981 | Noiles . |
| 4,316,468 | 2/1982 | Klieman et al. . |
| 4,325,376 | 4/1982 | Klieman et al. . |
| 4,325,377 | 4/1982 | Boebel . |
| 4,335,928 | 6/1982 | Barrett et al. . |
| 4,338,947 | 7/1982 | Williams . |
| 4,367,746 | 1/1983 | Derechinsky . |
| 4,372,316 | 2/1983 | Blake, III et al. . |
| 4,374,523 | 2/1983 | Yoon . |
| 4,393,883 | 7/1983 | Smyth et al. . |
| 4,412,539 | 11/1983 | Jarvik . |
| 4,425,915 | 1/1984 | Ivanov . |
| 4,430,997 | 2/1984 | DiGiovanni et al. . |
| 4,440,170 | 4/1984 | Golden et al. . |
| 4,450,839 | 5/1984 | Transue . |
| 4,452,357 | 6/1984 | Klieman et al. . |
| 4,452,376 | 6/1984 | Klieman et al. . |
| 4,471,780 | 9/1984 | Menges et al. . |
| 4,479,489 | 10/1984 | Tucci . |
| 4,480,641 | 11/1984 | Failla et al. . |
| 4,481,952 | 11/1984 | Pawelec . |
| 4,492,232 | 1/1985 | Green . |
| 4,505,414 | 3/1985 | Filipi . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,549,544 | 10/1985 | Favaron . |
| 4,550,715 | 11/1985 | Santangelo et al. . |
| 4,557,263 | 12/1985 | Green . |
| 4,558,706 | 12/1985 | Nakada et al. . |
| 4,562,839 | 1/1986 | Blake, III et al. . |
| 4,572,183 | 2/1986 | Juska . |
| 4,576,166 | 3/1986 | Montgomery et al. . |
| 4,589,421 | 5/1986 | Ullman . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,633,882 | 1/1987 | Matsuo et al. . |
| 4,646,740 | 3/1987 | Peters et al. . |
| 4,649,904 | 3/1987 | Krauter et al. . |
| 4,662,373 | 5/1987 | Montgomery et al. . |
| 4,662,374 | 5/1987 | Blake, III . |
| 4,674,501 | 6/1987 | Greenburg . |
| 4,674,504 | 6/1987 | Klieman et al. . |
| 4,682,491 | 7/1987 | Pickard . |
| 4,691,853 | 9/1987 | Storace . |
| 4,700,694 | 10/1987 | Shishido . |
| 4,712,549 | 12/1987 | Peters et al. . |
| 4,759,364 | 7/1988 | Boebel . |
| 4,784,137 | 11/1988 | Kulik et al. . |
| 4,841,888 | 6/1989 | Mills et al. . |
| 4,850,350 | 7/1989 | Jackson . |
| 4,850,355 | 7/1989 | Brooks et al. . |
| 4,858,608 | 8/1989 | McQuilkin . |
| 4,874,364 | 10/1989 | Morris et al. . |
| 4,900,307 | 2/1990 | Kulli . |
| 4,919,152 | 4/1990 | Ger . |
| 4,935,010 | 6/1990 | Cox et al. . |
| 4,944,443 | 7/1990 | Oddsen et al. . |
| 5,026,379 | 6/1991 | Yoon . |
| 5,030,226 | 7/1991 | Green et al. . |
| 5,040,715 | 8/1991 | Green et al. . |
| 5,049,152 | 9/1991 | Simon et al. . |
| 5,084,057 | 1/1992 | Green et al. . |
| 5,100,418 | 3/1992 | Yoon et al. . |
| 5,100,420 | 3/1992 | Green et al. . |
| 5,104,394 | 4/1992 | Knoepfler . |
| 5,104,395 | 4/1992 | Thornton et al. . |
| 5,112,343 | 5/1992 | Thornton . |
| 5,171,247 | 12/1992 | Hughett et al. . |
| 5,171,249 | 12/1992 | Stefanchik et al. . |

OTHER PUBLICATIONS

"Edward Weck Advertisement", *Surgery Gynecology & Obstetrics*, Spring 1986.

"Information About Dimethyl Silicone compounds," Dow Corning, 1988.

"Laparoscopic Sterilization with Electrocautery, Spring-Loaded Clips, and Silastic Bands: Technical Problems and Early Complications," Fertility and Sterility, vol. 27, No. 3, Mar. 1976.

"A Clip Applicator for Laparoscopic Sterilization," Fertility and Sterility, vol. 27, No. 9, Sep. 1976.

"Laparoscopic Sterilization with Spring-Loaded Clips: Double-Puncture Technique," The Journal of Reproductive Medicine, vol. 18, No. 5, May 1977.

"Laparoscopic Sterilization with the Spring Clip: Instrumentation Development and Current Clinical Experience," American Journal of Obstetrics and Gynecology, vol. 135, No. 8, Dec. 15, 1979.

Karl Storz Endoscopy-America Promotional Advertisement, "It's Your Choice for Tubal Sterilization," 1981.

"An Applicator for the Hulka Fallopian Tube Clip," American Journal of Obstertrics and Gyncecology, vol. 139, No. 6, Mar. 1981.

"Metal Clip Techniques Utilizing Pistol Grip Appliers," The American Journal of Surgery, Feb. 1982.

"Results of Experiment Endoscopic Esophagel Varix Ligation," the American Surgeon, Jan. 1988.

SURGICAL CLIP APPLIER HAVING CLIP ADVANCEMENT CONTROL

BACKGROUND OF THE INVENTION

1. Field of the Invention

This invention relates to an apparatus for applying surgical clips to body tissue during laparoscopic or endoscopic procedures, and more particularly, to a surgical clip applier configured for selective operation such that in a first mode the feed of a clip into the jaws is initiated by the user and in a second mode it is initiated independent of the user.

2. Description of Related Art

In laparoscopic and endoscopic surgical procedures, a small incision is made in the patient's body to provide access for a tube or cannula device. Once extended into the patient's body, the cannula allows insertion of various surgical instruments for acting on organs, blood vessels, ducts, or body tissue within the body cavity. Often during these procedures, it is necessary to apply hemostatic clips to blood vessels or ducts to prevent the flow of body fluids therethrough. Instruments for performing endoscopic surgical clip application are known in the art, and include both single clip and multiple clip appliers.

Endoscopic multiple clip appliers known in the art are described in U.S Pat. Nos. 5,084,057 and 5,100,042, the disclosures of which are incorporated herein by reference. In a commercially available embodiment of the invention of the '057 and '420 patents, the Auto Suture* Endo Clip* applier, a clip pusher is provided for individually advancing a clip from an array of stored clips towards a pair of distal jaw members. As each clip is formed by the jaw members, the clip pusher is drawn proximally to a position proximal to the distal-most clip in the clip array. The clip pusher is maintained in this position by a catch mechanism in the frame of the apparatus. At a desired time, the user of the instrument releases the catch mechanism, e.g., by actuating a trigger associated with the frame, thereby freeing the clip pusher to feed the distal-most clip into the jaw members. Thereupon, the jaw members may again be closed to form the clip. The maintenance of the clip pusher in a position proximal to the next clip until the user releases the catch mechanism is advantageous for several reasons, including the fact that the jaws will be empty of a clip for tissue dissection and for passage into and out of a trocar sleeve.

Another multiple clip applier for use in an endoscopic surgical procedure is disclosed in U.S. Pat. No. 5,112,343 to Thornton. As with the commercially available Endo Clip* applier, the Thornton device includes a mechanism which enables the user to select the point in time when a clip is to be advanced to the jaws. The mechanism includes a button 100 which is pressed by the user to release a drive link to feed a clip into the jaws. The Thornton device is intended, inter alia, to reduce the risk that a clip waiting in the jaws may be dislodged and fall into the body (see col. 1, lines 44–59).

A second commercially available endoscopic multiple clip applier, the Ethicon Ligaclip, duplicates the structure, function and use of the Endo Clip* applier with one exception, the catch mechanism in the frame is omitted. Thus, after a clip is formed by the jaws, the clip pusher places the next clip in the jaws without further action by the user. Although offering the potential for relatively small time savings during a surgical procedure, the Ligaclip suffers from the disadvantage that a clip is present in the jaws at all times, including times when the user would prefer that the jaws be empty.

It is an object of the subject invention to provide a surgical clip applier for applying multiple clips during endoscopic or laparoscopic procedures which is configured for selective operation, such that in a first mode the feed of a clip into the jaws is initiated by the user and in a second mode it is initiated independent of the user.

It is another object of the subject invention to provide a surgical clip applier for applying multiple clips during endoscopic or laparoscopic procedures which provides the user with a mechanism for selecting between the two modes of operation described above.

These and other objects of the subject invention will become more readily apparent from the following description of the invention.

SUMMARY OF THE INVENTION

An apparatus is disclosed for applying surgical clips which comprises a handle portion, a body portion which extends distally from the handle portion, jaw members positioned adjacent the distal end of the body portion for receiving and subsequently forming a clip, camming means which are operable from the handle portion for camming the jaw members closed to form a clip, storage means for storing a plurality of surgical clips in a position for individual advancement to the jaw members, clip advancement means for individually advancing the clips from the storage means into the jaw members, and control means for selecting between a first mode of operation in which the advancement of a clip from the storage means into the jaw members is initiated by the user and a second mode in which it is initiated independent of the user.

The clip advancement means includes a clip pusher which is at least partially positioned within the body portion of the apparatus. A pusher structure is associated with the clip pusher and is positioned within the handle portion of the apparatus. The control means includes lock means associated with the handle portion that, when properly oriented, releasably locks the pusher structure such that, after a clip is formed by the jaw members, the clip pusher is maintained in a position proximal to the distal-most clip in the storage means. The control means is adapted to be moved between a first position in which the lock means is oriented to releasably lock the pusher structure after a clip is formed by the jaw members ("interactive mode"), and a second position in which the lock means is oriented so as not to releasably lock the pusher structure, i.e., the pusher structure moves independent of the lock means ("non-interactive mode").

When the control means is positioned such that the lock means is in the interactive mode, advancement of a clip into the jaw members is initiated by the user releasing the lock means. In the non-interactive mode, however, advancement of a clip into the jaw members is independent of the user. Movement of the control means between the first and second positions results in corresponding changes to the apparatus' mode of operation.

In one embodiment of the invention, a first release means is associated with the handle portion of the apparatus for manually releasing the lock means to permit the clip pusher to advance a clip into the jaw members.

For example, the first release means may comprise a release trigger which is actuated by the user (with the lock means in the interactive mode) to release the lock means from engagement with the pusher structure. The release trigger may be mounted to a release lever which is movable in a longitudinal direction for releasing the lock means. In another preferred embodiment, the first release means comprises a toggle switch having a detent which is biased into releasable engagement with the pusher structure.

The apparatus may further comprise second release means associated with the camming means for releasing the lock means (independent of the user) when the lock means is in the non-interactive mode, thereby permitting the clip pusher to advance a clip into the jaw members. More particularly, the second release means may comprise a proximal extension to channel structure associated with the camming means. The camming means is movable in a longitudinal direction between a proximal position wherein the jaw members are in a clip receiving position and a distal position wherein the jaw members are in a clip forming position. The proximal extension to the channel structure is configured for releasing the lock means when the camming means is in its proximal position which corresponds to the jaw members being in the clip receiving position.

In a further embodiment, the control means includes a sliding selector switch which is associated with the handle portion and which is configured for movement between a first position wherein the first release means is enabled and a second position wherein the second release means is enabled.

Further features of the subject invention will become more readily apparent from the following detailed description of the preferred embodiments taken in conjunction with the accompanying drawings.

BRIEF DESCRIPTION OF THE DRAWINGS

Preferred embodiments of the surgical apparatus of the subject invention will be discussed hereinbelow with respect to drawings wherein.

DETAILED DESCRIPTION OF THE PREFERRED EMBODIMENTS

Because endoscopic procedures are more common than laparoscopic procedures, the present invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to laparoscopic procedures. In that regard, applicants specifically refer to and incorporate herein the description of sealing means set forth in U.S. Pat. Nos. 5,084,057, and 5,100,420, the contents of which were previously incorporated herein in their entireties.

In the drawings and in the description which follows, the term "proximal", as is traditional, will refer to the end of the apparatus which is closest to the operator, while the term "distal" will refer to the end which is furthest from the operator.

Figure 1:
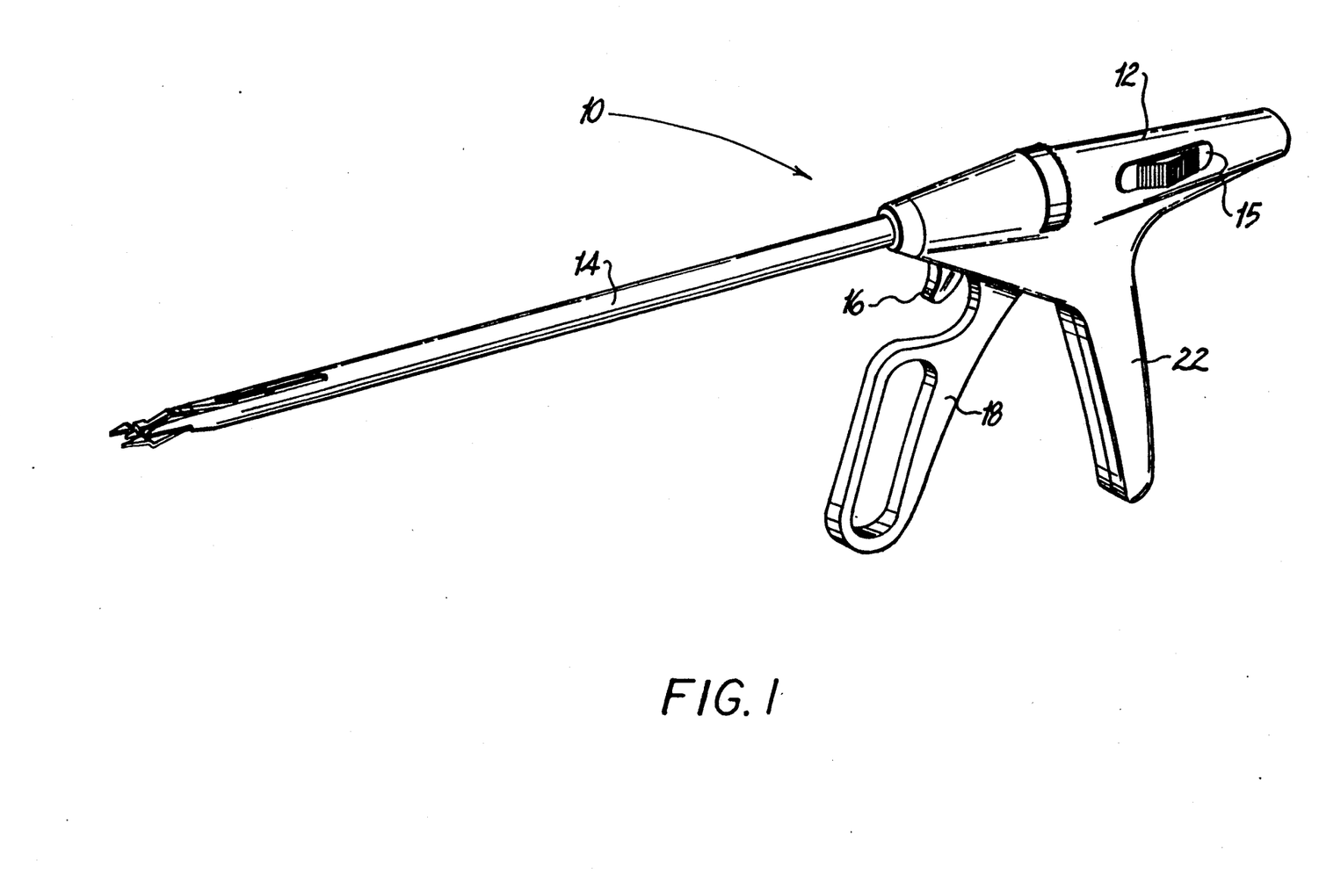
FIG. 1 is a perspective view of a surgical apparatus in accordance with a preferred embodiment of the subject invention.

Referring now in detail to the drawings in which like reference numerals identify similar or identical elements, a preferred embodiment of the surgical apparatus of the subject invention is illustrated in FIG. 1, and is designated generally by reference numeral 10. In brief, surgical apparatus 10 includes a handle portion 12 and an elongated body portion 14 defining a longitudinal axis which extends distally from the handle portion 12. Apparatus 10 is configured for selective operation in a user-initiated mode or a user-independent mode through user manipulation of a selector switch 15 which is associated with handle portion 12. In the user-initiated mode of operation, surgical clips are individually advanced from the clip storage means into jaw members 24 in response to manipulation of a release trigger 16. In the user-independent mode of operation, a surgical clip is individually advanced from the clip storage means into jaws 24 each time the previous clip is formed by the jaw members (until the clip supply is depleted).

Figure 2:
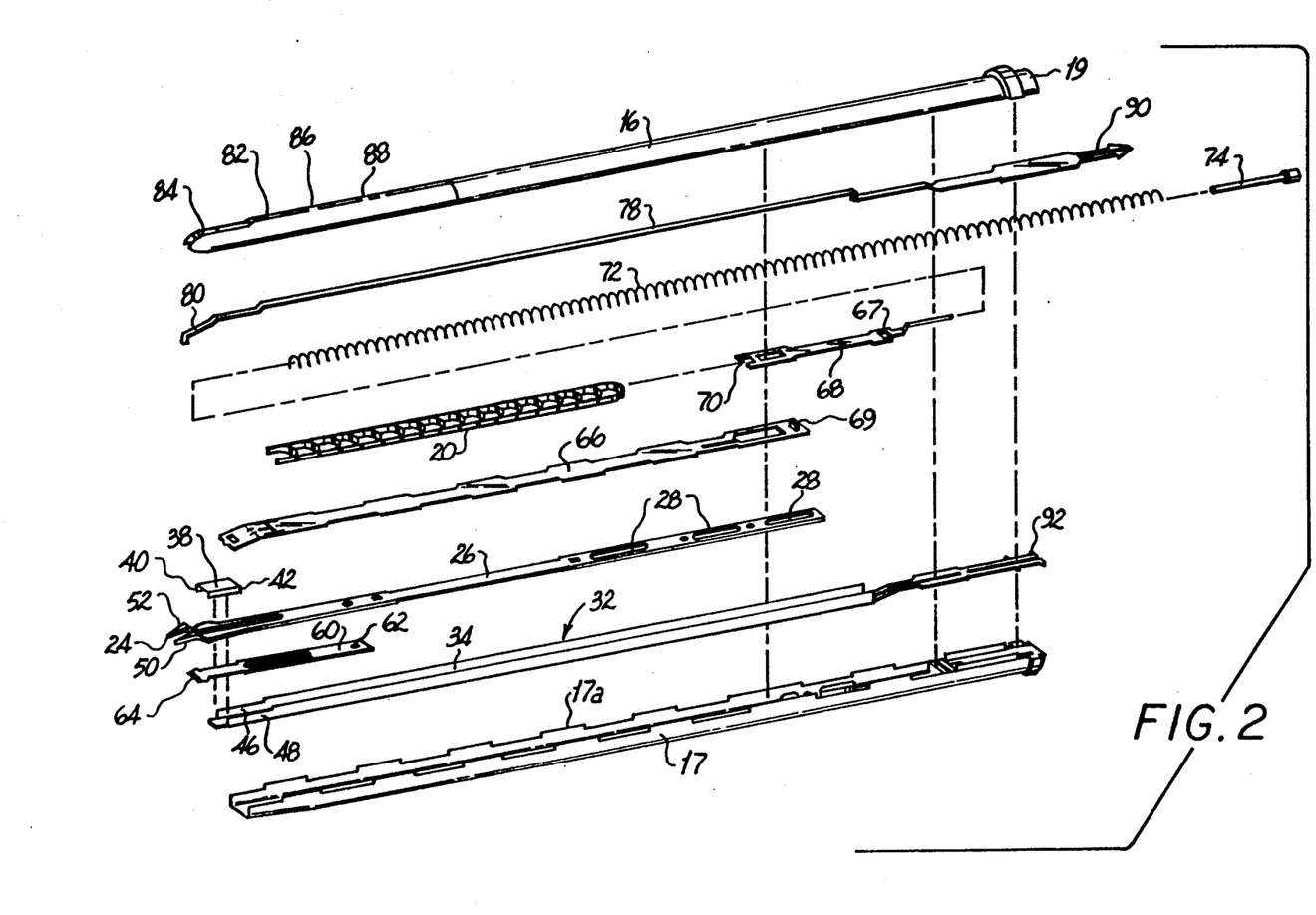
FIG. 2 is an exploded perspective view of the body portion of the surgical apparatus of FIG. 1.

Referring now to FIG. 2, the elongated body portion 14 of surgical apparatus 10 is preferably comprises an upper hemi-section 16 and a lower hemi-section 17. Elongated body portion 14 is preferably integral with handle portion 12, although it can be constructed to be removable from the handle portion 12 (see, e.g., U.S. Pat. No. 5,100,420, previously incorporated by reference). The upper and lower hemi-sections 16, 17 are formed of a material that is capable of withstanding the stresses applied by the internal components of the apparatus without deformation or compromise of precision. A polycarbonate material such as LEXAN brand material which is marketed by General Electric Corporation has been found to satisfy the strength and deformation requirements.

The lower hemi-section 17 of the cartridge includes upstanding tabs 17a while the upper hemi-section 16 includes corresponding slots (not shown) which are dimensioned and configured to receive the upstanding tabs 17a such that the two hemi-sections may be attached by ultrasonic welding techniques. Preferably, the slots are dimensioned to receive the upstanding tabs 17a in interference relationship to assist in their securement. However, the hemi-sections may be attached by adhesives or by other known means. In addition, the proximal end of upper hemi-section 16 is provided with a slotted area 19 adapted for engagement with a mechanism disposed within handle portion 12 which facilitates rotation of the elongated portion 14 about the longitudinal axis thereof to increase the range of operability of the instrument. Sealing means for obstructing passage of gas through the apparatus, e.g., a sealing block and/or silicone grease, as described in U.S. Pat. Nos. 5,084,057 and 5,100,420, previously incorporated by reference, is positioned within the apparatus, preferably toward the proximal end of body portion 14.

A plurality of surgical clips 20 are positioned within the cartridge and are disposed in a manner for advancement toward a distal end thereof. The clips are of generally U-shaped configuration and are aligned in a row with the leg portions thereof facing distally. Preferably, the clips are made of titanium which is a material well suited for ligating or clamping blood vessels. A jaw blade 26 is positioned at the distal end of body portion 14 and includes resilient jaw members 24 dimensioned for reception of the surgical clips 20. Jaw blade 26 is fabricated of a material having a sufficient resiliency to facilitate the relative movement of jaws 24 towards one another to close a clip therebetween, followed by return of the jaws 24 to an original position upon release of clamping forces. Stainless steel has been found to be a suitable material which is capable of withstanding the requisite number of clamping cycles without adverse effect. Jaw blade 26 is formed with a plurality of spaced apart apertures 28 which are dimensioned to receive a plurality of corresponding pins or columnar extensions (not shown) molded into the lower hemi-section 17 for positioning the jaw blade 26 with respect to the elongated body portion 14 of the instrument.

As best seen in FIG. 2, a crimping channel 32, which is dimensioned and positioned for slidable movement within body portion 14, defines an elongated channel 34. A channel bracket 38, preferably of stainless steel, is disposed above jaw blade 26 and defines a pair of depending side walls 40 and 42 which are positioned to be welded to the distal portions of correspondingly positioned and dimensioned upwardly extending side walls 46 and 48 associated with crimping channel 32. Once assembled, crimping channel 32 and channel bracket 38 altogether form a slidable housing of rectangular configuration which surrounds jaw blade 26. Moreover, since the jaw members 24 of jaw blade 26 each have outwardly tapered side walls 50 and 52, respectively, movement of the crimping channel 32 in a distal direction will cause inward movement of jaw members 24 through a camming action, while movement of the crimping channel in the proximal direction will result in corresponding proximal movement of channel bracket 38, thereby relieving the camming forces from jaw members 24 and permitting jaw members 24 to resiliently open to their relaxed condition.

A tissue stop plate 60 is positioned between jaw blade 26 and crimping channel 32, and includes an aperture 62 at the proximal end portion thereof dimensioned for reception of a corresponding pin (not shown) which extends through jaw blade 26 and tissue stop plate 60 to maintain relative alignment therebetween. At the distal portion of the tissue stop plate 60, a tab 64 is oriented at approximately the same angle as jaws 24 for alignment therewith, and includes an arcuate cut-out portion which is dimensioned to receive a blood vessel.

Referring still to FIG. 2, a cover plate 66 is appropriately dimensioned to rest upon the jaw camming mechanism described hereinabove, and supports the row of surgical clips 20 disposed in body portion 14. A clip follower 68 is positioned proximal to the surgical clips 20 and has a U-shaped distal end portion 70 configured for engaging and distally advancing clips 20 under the action of a clip feed spring 72. Feed spring 72 is connected at the proximal end thereof by a pin 74 which is in turn connected to cover plate 66 by an anchor tab 69.

A clip pusher 78 is positioned for longitudinal movement with respect to cover plate 66 between a proximal position and a distal position. Engagement of the distal-most clip by pusher bar 78 is facilitated through the distal nose 80 of clip pusher bar 78. Movement of clip pusher bar 78 between a proximal position and a distal position results in positioning of nose 80 behind successive clips 20 and individual advancement of successive clips 20 into jaws 24 of jaw blade 26.

The upper hemi-section 16 of body portion 14 includes a longitudinal slot 82 having a plurality of bridge connections 84, 86, and 88 provided therein. Clip pusher bar 78 is adapted to be intermeshed with the bridges and, in particular, to be positioned above proximal bridge 88 and below distal bridges 86 and 84, such that proximal bridge 88 acts as a stop mechanism to prevent advancement of the clip follower 68 when an upstanding tab 67 comes into engagement with bridge 88. This engagement will occur when the last clip 20 in the body portion 14 has been advanced and crimped, thereby permitting the clip follower 68 to advance to its distal-most position under action of spring 72.

Figure 3:
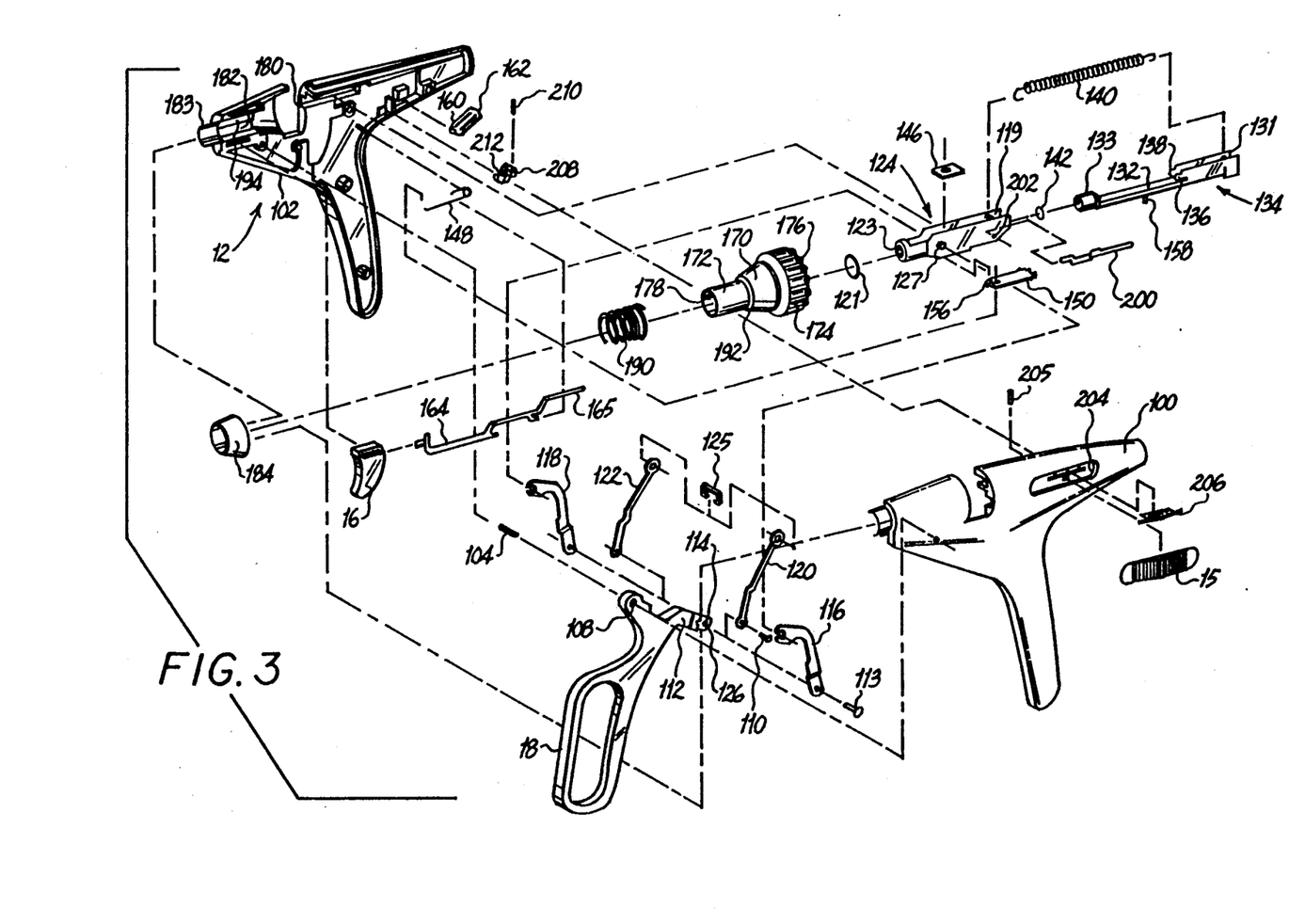
FIG. 3 is an exploded perspective view of the handle portion of the surgical apparatus of FIG. 1.

Clip pusher 78 and crimping channel 32 are each operatively connected to structure within handle portion 14 which facilitate their respective actions during use of apparatus 10. In particular, proximal end portion 90 of clip pusher 78 and proximal end portion 92 of crimping channel 32 each cooperate with structure within handle portion 12. Turning now to FIG. 3, the handle portion 12 comprises opposed right and left hemi-sections 100 and 102 which are mounted to one another by fasteners or, in the alternative, the hemi-sections may be sonically welded or adhesively attached to one another. Preferably, the right and left hemi-sections 100 and 102 of handle portion 12 are fabricated of a hard plastic material such as LEXAN brand material, although the use of other rigid material is envisioned.

Pivoting handle 18 is mounted through an aperture 108 on a pin 104 which extends transversely therethrough. Handle 18 includes a rearward extension 112 having an arcuate slot 126 defined therein through which a pivot pin 110 extends. Another pin 113 extends through an aperture 114 in extension 112 and functions as a pivot for a left channel link 116 and a right channel link 118 which extend in a generally forward direction. A left pusher link 120 and a right pusher link 122 are also provided and are mounted for pivotal movement on pin 110. The opposed ends of left channel link 116 and right channel link 118 are pivotably mounted to a channel tube 124 by opposed pivot pins, of which pivot pin 127 is one, which are formed integral therewith. Pusher links 120 and 122 are connected to a C-shaped clasp 125 which is arranged for engagement with spaced apart notched shoulders 136 and 138 formed in a pusher tube 134. Thus, manipulation of pivoting handle 18 will cause corresponding translation of pusher links 120 and 122 in a generally proximal direction, urging the pusher tube 134 proximally within handle portion 12. A main spring member 140 operatively connects channel tube 124 with pusher tube 134. In particular, a pin 119 connects the distal end of main spring 140 to channel tube 124 while a pin 131 connects the proximal end thereof to pusher tube 124. Spring 140 is thus loaded when channel tube 124 and pusher tube 134 are separated by movement of pivoting handle 18 toward handle grip portion 22 which causes distal movement of channel tube 124 and relative proximal movement of pusher tube 134.

When a surgical clip 20 has been positioned within the jaws 24 of jaw blade 26, manipulation of pivoting handle 18 towards hand grip 22 will cause distal and pivotal movement of channel links 116 and 118, resulting in distal movement of channel tube 124 and corresponding distal movement of crimping channel 32. This action causes channel bracket 38, together with crimping channel 32 to engage and move the jaw members 24 of jaw blade 26 toward one another, thereby forming the surgical clip 20 positioned therebetween.

Pusher tube 134 is connected to clip pusher bar 78 by proximal end tabs 90 which are inserted into the distal opening 133 of pusher tube 134. An annular steel pad 142 is positioned between the two members to define an interface therebetween. Similarly, crimping channel 32 is connected to channel tube 124 by insertion of the proximal legs 92 thereof into the distal opening 123 of channel tube 124, with an annular steel pad 121 positioned as an interface therebetween. As a result, the crimping channel 32 and clip pusher bar 78 are free to rotate independent of channel tube 124 and pusher tube 134 since their respective proximal legs 90 and 92 are disposed within the distal opening 133 of pusher tube 134 and opening 123 of channel tube 124. The benefit of this independent rotational feature will be discussed in greater detail hereinbelow with respect to a mechanism for rotating the body portion 14 of the surgical apparatus 10 about its longitudinal axis.

As best seen in FIG. 3, a latch plate 150 is pivotably mounted and biased upward toward an aperture plate 146 disposed in the lower wall of channel tube 124 by a spring 148 such that a tongue 156 formed on latch plate 150 engages the aperture plate 46 when channel tube 124 is moved to its proximal position. Engagement of channel tube 124 by latch plate 150 prevents forward movement of the channel tube 124 prior to the advancement of a clip 20 into the opposed jaw members 24 of jaw plate 26. Release of tongue 156 is accomplished by a detent 158 which depends from pusher tube 134 and which disengages latch plate 150 when pusher tube 134 is moved distally under the influence of main spring 140.

A mechanism is also provided for releasably locking the pusher tube 134 in a proximal position against the influence of main spring 140. The mechanism includes a pusher release member 160, configured as a leaf spring, disposed within handle portion 12 and having a tab 162 configured to engage a slot 161 formed in the bottom wall of pusher tube 134 when pusher tube 134 is moved proximally by pusher links 120 and 122 against the force of the main spring 140. This mechanism cooperates with a release trigger 16, in an interactive mode of operation, to initiate placement of a clip 20 in jaw members 24 when desired by the user. The mechanism also prevents premature advancement of the distal-most clip 20 into the jaws 24 of jaw blade 26 which could result in a dropped clip or in unwanted deformation of the clip.

In the interactive mode, liberation of the pusher release member 160 is accomplished by proximal movement of a release lever 164 via user actuation of release trigger 16. Lever 164 is supported at the proximal end 165 thereof by a support block 168 formed integral with the right hemi-section 102 of handle portion 12. In the non-interactive mode of operation, the liberation of pusher release member 160 is accomplished by proximal movement of a proximal extension 200 which is mounted to channel tube 124 through an aperture 202 provided at the proximal end thereof.

To select between the interactive and non-interactive modes of operation, the user may manipulate selector switch 15 in a longitudinal direction within a slotted area 204 between a first position in which the release mechanism associated with trigger 15 is enabled (interactive mode) and a second position in which the proximal extension 200 from channel tube 124 is enabled (non-interactive mode). A cam member 206 is operatively associated with selector switch 15 through a pin 205 and moves longitudinally therewith to translate a control block 208. Control block 208 is associated with selector switch 15 through a cam follower pin 210 and is configured to move along a path which is transverse to the longitudinal axis of the instrument as the selector switch 15 is moved longitudinally. A groove 212 is formed through control block 208 for permitting the passage of the proximal end 165 of release lever 164.

In use, when the operator has positioned selector switch 15 in the position which corresponds to the interactive mode of operation, control block 208 permits lever 164 to come into contact with pusher release member 160. Conversely, control block 208 acts to deflect proximal extension 200 from its operational position, preventing proximal extension 200 from contacting pusher release member 160 as channel tube 124 moves proximally to facilitate liberation of pusher tube 134. When the user desires non-interactive operation of apparatus 10, movement of the selector switch 15 to a second position will cause control block 208 to translate transversely so as to permit proximal extension 200 to return to an operational position. In this orientation of selector switch 15, lever 164 will remain in a position for contacting pusher release member 160 although its impact will be overshadowed by the movement of proximal extension 200, i.e., proximal extension 200 will contact release member 160 prior to and independent of lever 164, making lever 164 a redundant structure for this mode of operation.

Manipulation of pivoting handle 18 toward handle grip 22 causes pusher links 120 and 122 to pivot and move in a generally proximal direction resulting in proximal movement of pusher tube 134 by engagement of C-shaped clasp 125 with the shoulders 136 and 138 of pusher tube 134. Proximal movement of pusher tube 134 will continue with pusher release member 160 continuously biased upward until tab 162 enters the slot 161 in the bottom wall of pusher tube 134, thereby retaining pusher tube 134 in a desired position against the influence of main spring 140. Proximal movement of pusher tube 134 withdraws clip pusher 78 to a position proximal of the distal-most clip 20 in body portion 14, thereby positioning clip pusher 78 for advancement of the distal-most clip 20 into the jaw members 24 of the jaw blade 26. Retention of the pusher tube 134 in a proximal position by release member 160 also retains clip pusher 78 in a corresponding position until the distal-most clip 20 is to be advanced into the jaws.

When the instrument is in the interactive mode, proximal movement of release trigger 16 by the user at a desired time will cause release lever 164 to disengage pusher release member 160 from pusher tube 134, thereby releasing pusher tube 134. As a result, pusher tube 134 and clip pusher bar 78 move distally under the bias of main spring 140, advancing the distal-most clip 20 into the jaws 24 of jaw blade 26.

When surgical apparatus 10 is in the non-interactive mode of operation, proximal movement of pusher tube 134 proceeds as in the interactive mode, i.e., in response to proximal movement of pusher links 120 and 122. Pusher release member 160 is biased upward and tab 160 enters slot 161 in the bottom wall of pusher tube 134 when it becomes aligned therewith, thereby retaining pusher tube 134 in a proximal position against the influence of main spring 140. After a surgical clip 20 is formed by jaws 24, channel tube 124 is drawn in the proximal direction by main spring 140, thereby bringing proximal extension 200 into contact with pusher release member 160. Proximal extension 200 releases pusher release member 160 from contact with pusher tube 134, thereby allowing pusher tube 134 to travel in a distal direction under the influence of main spring 140, advancing the distal-most clip 20 into the jaws 24 of jaw blade 26.

As stated briefly above, the surgical instrument of the subject invention is provided with structure for deactivating the clip forming mechanism after all of the clips have been dispensed from the body portion 14 to promote safe operation. As best seen in FIG. 2, this safety feature is achieved through interaction of the clip follower 68 with the bridge 88 formed in the upper hemi-section 15 of the cartridge. In particular, the upstanding tab 67 which is provided on the proximal portion of clip follower 68 is dimensioned to engage bridge 88 when clip follower 68 has assumed its distal-most position under the influence of spring 72. This engagement prevents further distal movement the clip follower 68. Additionally, a slot 65 is defined at the distal portion of clip follower 68 which is positioned to engage the nose 80 of clip pusher 78 when the clip follower 68 has advanced to its distal-most position. This engagement prevents further distal movement of clip pusher 78 and pusher tube 134, thus maintaining channel tube 124 locked in its proximal-most position by the tongue 156 of latch plate 150. As a result, further manipulation of pivoting handle 18 toward handle grip 22 is prevented, thereby safely deactivating the clip forming mechanism of the subject invention.

Referring once again to FIG. 2, the surgical apparatus of the subject invention is provided with a mechanism for rotating the elongated body portion 14 of the instrument about the longitudinal axis thereof relative to the handle portion 12. To accomplish this movement, a rotating collar 170 is provided which is constructed of the same material as the handle, and which includes a distal cylindrical nose section 172 and a proximal barrel section 174. A proximal face of the barrel section 174 is formed with a plurality of proximally extending teeth 176 positioned circumferentially thereabout. The cylindrical nose section 172 includes an inwardly extending rib 178 at the distal end thereof, which, in the assembled condition, rests within the cylindrical distal opening 182 of the distal end of the handle portion 12. In addition, a nose piece 184 is fitted over the distal cylindrical end 183 of handle portion 12.

A coiled spring 190 is positioned between the shoulders 192 of collar 170 and shoulders 194 which are formed in the body of handle portion 12 to bias the rotatable collar 170 in the proximal direction causing engaging teeth 185 formed in handle portion 12 to engage with the circumferential teeth 176 of collar 170. This engagement effectuates fixation of the rotatable orientation of collar 170. The distal cylindrical section 172 of collar 170 includes a cylindrical opening which is dimensioned to receive the proximal end of the elongated body portion formed of upper and lower hemi-sections 16 and 17, with a distally positioned tooth 178 positioned to engage the longitudinally extending groove 19 provided in upper hemi-section 16 to cause the body portion 14 to rotate with collar 170. In addition, the proximal legs 90 of clip pusher bar 78 are permitted to rotate within the distal end portion 133 of pusher tube 134 and the proximal legs 92 of the crimping channel 32 are permitted to rotate within the distal end portion 123 of channel tube 124. As a result, the entire elongated body portion 14 of surgical apparatus 10 may be selectively rotated by the user through pushing collar 170 in a distal direction sufficient to disengage tooth 180 on the body portion 12 and subsequently rotating collar 170 until the body portion 14 reaches a desired angular orientation. Thereafter, by releasing collar 170 the bias of coiled spring 190 will cause collar 170 to return to an unbiased and locked position.

Figure 4:
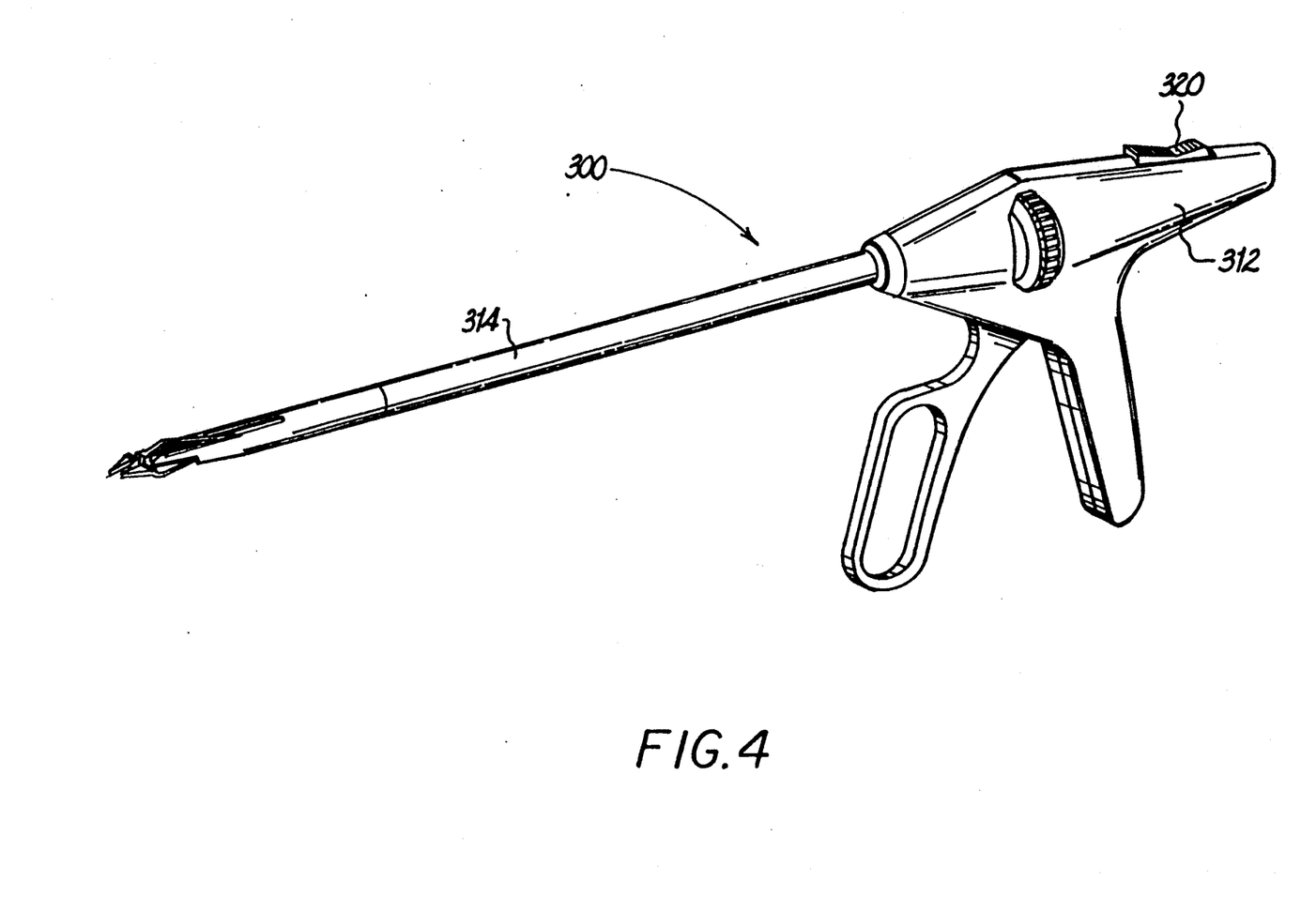
FIG. 4 is a perspective view a surgical apparatus in accordance with another preferred embodiment of the subject invention.

Another preferred embodiment of the surgical apparatus of the subject invention is illustrated in FIG. 4, and is designated generally by reference numeral 300. Briefly, surgical apparatus 300 comprises a handle portion 312, and an elongated body portion 314 which extends distally from the handle portion 312. The body portion 314 is identical to the structure described in connection with the first embodiment and is configured for storing a plurality of surgical clips in a position for individual advancement toward jaw members disposed at the distal end thereof. Surgical apparatus 300 differs from surgical apparatus 100 described hereinabove in the omission of a trigger (see trigger 16 in FIG. 1) and in the structure for selectively controlling the clip advancement structure.

Figure 5:
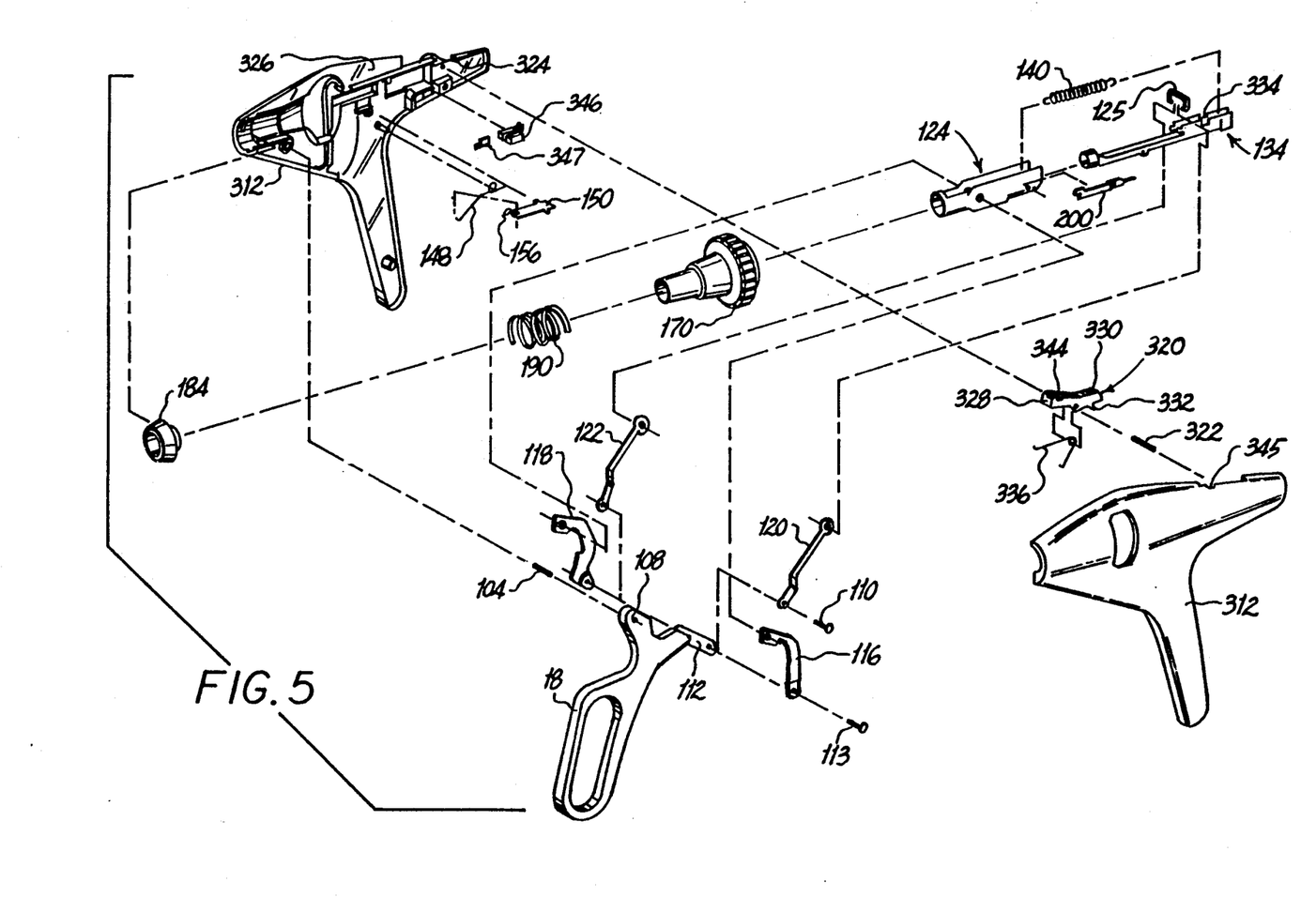
FIG. 5 is an exploded perspective view of the handle portion of the surgical apparatus of FIG. 4.

Referring to FIG. 5, the control structure of surgical apparatus 300 comprises a toggle switch 320 which is pivotably mounted by a pivot pin 322 in a cavity 324 provided in the barrel section 326 of handle portion 312. Toggle switch 320 is defined by a distal portion 328 and a proximal portion 330. A detent 332 depends downwardly from the proximal portion 330 and is dimensioned and configured for releasably engaging a keeper notch area 334 which is formed in the pusher tube 134. A biasing spring 336, preferably in the form of a looped torsion spring, is positioned in cavity 324 proximate to the distal portion 328 of toggle switch 320. Biasing spring 336 imparts a biasing force on the toggle switch 320 which acts in a clockwise direction with respect to pivot pin 322. As a result, the proximal portion 330 of toggle switch 320 is urged into a position wherein detent 332 is engageable with the keeper notch area 334 of pusher tube 134.

Figure 6:
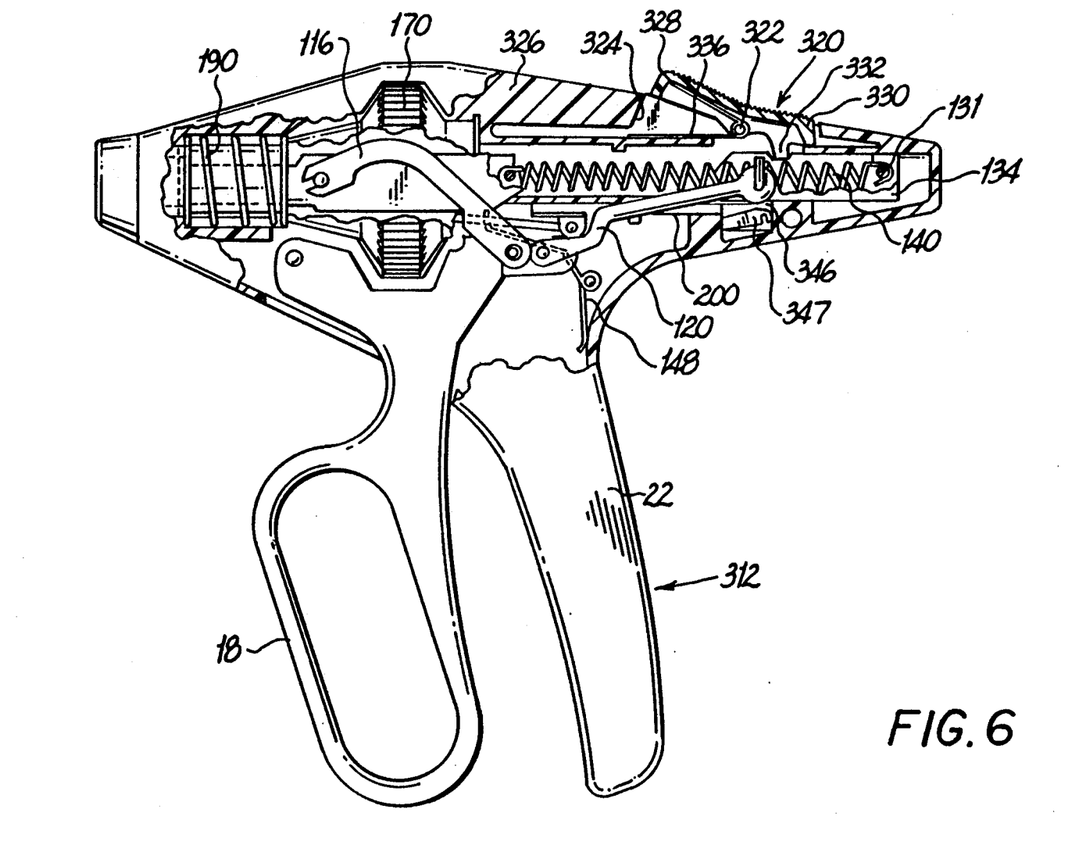
FIG. 6 is a side elevational view of the handle portion of the surgical apparatus of FIG. 4 in a manual mode of operation.

In operation and with toggle switch in its clockwise orientation (see FIG. 6), as pusher tube 134 traverses the barrel section 336 of handle portion 312 in a proximal direction under the influence of pusher links 340 and 342, as described in connection with surgical apparatus 10 hereinabove, detent 332 releasably engages the keeper notch area 334, thereby preventing pusher tube 134 from returning to its normal, distal position. Consequently, the clip advancement structure associated with pusher tube 134 remains in a pre-advancement position proximal to the distal-most clip 20 disposed within the body portion 314 of the instrument. With the toggle switch 320 in this clockwise orientation, surgical instrument 300 is in an interactive mode of operation. Accordingly, advancement of the distal-most clip 20 into the jaws associated with the distal end of the body portion 314 of the instrument does not occur until the user releases detent 332 from keeper notch 334 by manipulating toggle switch 320 counterclockwise. When toggle switch 320 is pivoted counterclockwise, pusher tube 134 is freed to translate distally under the bias of main spring 140, driving the clip advancement structure within the body portion 314 forward to advance the distal-most clip 20 into the jaws.

Figure 7:
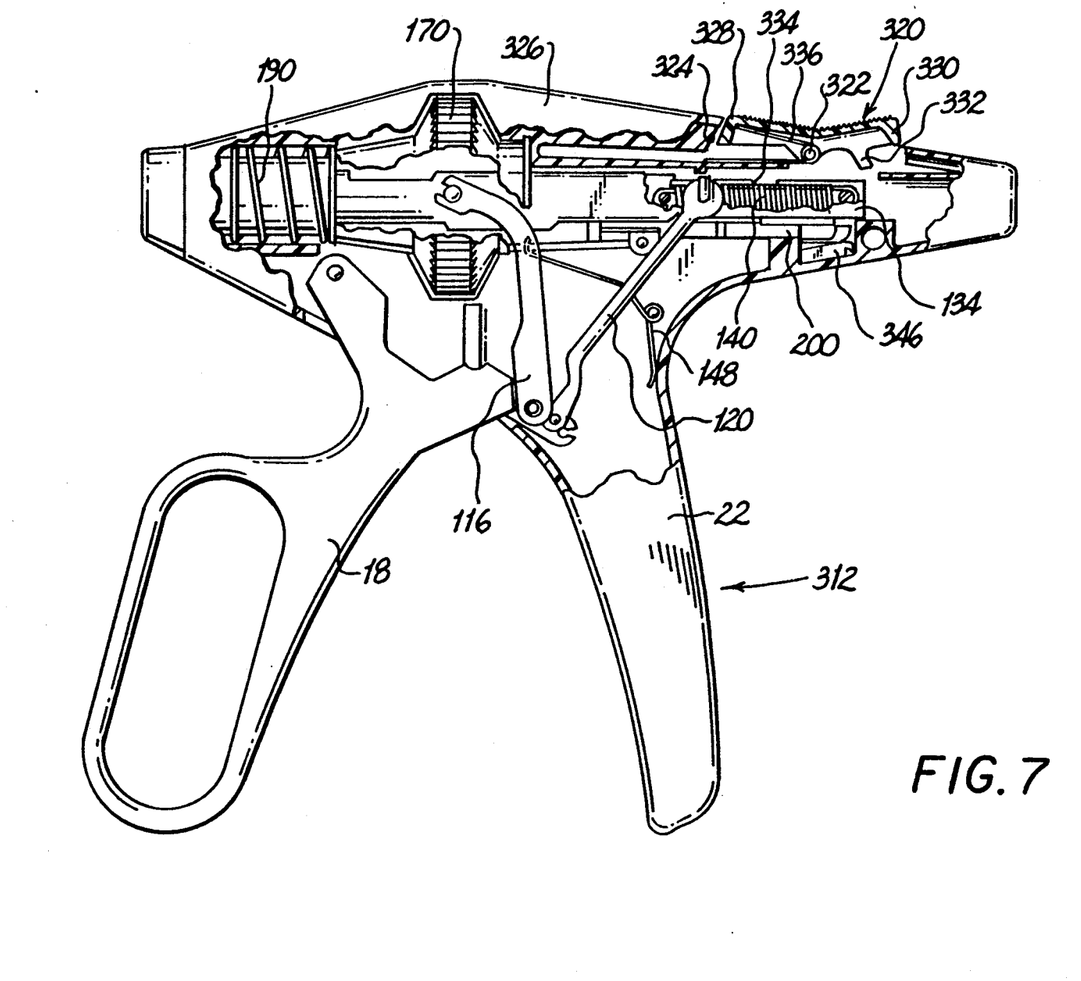
FIG. 7 is a side elevational view of the handle portion of the surgical apparatus of FIG. 4 in an automatic mode of operation.

Should the user of surgical apparatus 300 prefer at any point to operate the apparatus in a non-interactive mode, toggle switch 320 is pivoted counterclockwise to the position shown in FIG. 7. An abutment feature secures the toggle switch 320 in the counterclockwise orientation (against the bias of biasing spring 336) and includes a toggle catch 344 which is frictionally engageable within a port 345 formed in cavity 324 adjacent the proximal portion 330 of toggle switch 320 (see FIG. 5). The toggle catch 344 is configured to impart sufficient frictional retention forces on toggle switch 320 to prevent the biasing spring 336 from urging toggle switch 320 into the clockwise position shown in FIG. 6.

With toggle switch 320 in the counterclockwise position of FIG. 7, the instrument operates in the non-interactive manner described hereinabove with respect to apparatus 10. More particularly, as pusher tube 134 is drawn to its proximal-most position through actuation of pivotal handle 18, aperture plate 146 is engaged by a lock member 346 biased by spring 347, thereby maintaining pusher tube 134 in its proximal-most position. Subsequently, after forming a clip, channel tube 134 returns from its distal-most position under the influence of main spring 140 and proximal extension 200 disengages lock member 346 from aperture plate 146. Once lock member 346 is disengaged, pusher tube 134 is released to move under the bias of main spring 140. As a result, clip pusher 78 moves distally to advance the next clip 20 into the jaws.

The surgical apparatus of the present invention enjoys many clinical advantages. When operated in the interactive mode, the apparatus provides the advantages associated with the surgeon controlling the placement of a clip in the jaws. For example, the surgeon may operate the apparatus such that the jaws are free of a clip in desired instances, thereby facilitating dissection with the apparatus jaws and passage of the apparatus into and out of a trocar sleeve. When the apparatus is operated in the non-interactive mode, the apparatus provides for more rapid placement of clips into the jaws, e.g. when a plurality of clips are to be placed in rapid succession, as when being placed side-by-side on the same vessel. Allowing the surgeon to select between the two modes of operation is particularly advantageous in that the mode of operation of the device can be selected to suit the clinical situation at each instant in a surgical procedure.

Although the invention has been described with respect to preferred embodiments, it should be readily apparent to one of ordinary skill in the art that changes or modifications may be made without departing from the spirit or scope of the subject invention as defined by the appended claims.

What is claimed is:

1. An apparatus for applying surgical clips comprising:
   a) a handle portion;
   b) a body portion extending distally from said handle portion;
   c) jaw members positioned adjacent the distal end of the body portion and movable between an open position for receiving a clip and a closed position for forming the clip;
   d) camming means operable from the handle portion and cooperative with the jaw members for camming the jaw members closed to form the clip;
   e) storage means disposed within said body portion proximate the jaw members for storing a plurality of clips in a position for individual advancement to the jaw members;
   f) clip advancement means for individually advancing clips from the storage means into the jaw members; and
   g) control means operatively associated with said handle portion for selecting between a first mode in which advancement of a clip from said storage means to said jaw members is effectuated by manually releasing said clip advancement means from a preadvancement position and a second mode in which said clip advancement means is automatically released from said pre-advancement position as said jaw members move from said closed position to said open position.

2. An apparatus as recited in claim 1, wherein said clip advancement means comprises a clip pusher operatively disposed in said body portion.

3. An apparatus as recited in claim 2, wherein said control means includes means for releasably locking a pusher tube associated with said clip pusher in a locked position wherein said clip pusher is in a position proximal to a distal-most clip in said storage means corresponding to said pre-advancement position.

4. An apparatus as recited in claim 1, wherein said control means includes a selector for moving a locking mechanism operatively associated with said clip advancement means between an operational position and a non-operational position.

5. An apparatus as recited in claim 4, wherein said clip advancement means includes a clip pusher which cooperates with a pusher tube, said locking mechanism being configured to releasably engage said pusher tube when said locking mechanism is in said operational position.

6. An apparatus as recited in claim 5, further comprising a release trigger operatively associated with a release lever disposed in said handle portion, and release lever being movable in a longitudinal direction to release said locking mechanism from engagement with said clip pusher.

7. An apparatus as recited in claim 6, further comprising a channel tube associated with said camming means and having a proximal projection extending therefrom for releasing said locking mechanism from said non-operational position.

8. An apparatus as recited in claim 1, further comprising means for rotating said body portion about a longitudinal axis thereof relative to said handle portion.

9. An apparatus as recited in claim 8, wherein said means for rotating said body portion further comprises means for selectively maintaining said body portion at a predetermined angle of rotation relative to said handle portion.

10. An apparatus as recited in claim 1, wherein said control means includes a slide switch positioned on said handle portion and configured for longitudinal movement between a first position which corresponds to said first mode and a second position which corresponds to said second mode.

11. An apparatus according to claim 1, further comprising sealing means for obstructing the passage of gas through said body portion.

12. An apparatus according to claim 11, wherein said sealing means comprises a sealing block and silicone grease.

* * * * *